United States Patent [19]

Kami

[11] Patent Number: 4,549,550
[45] Date of Patent: Oct. 29, 1985

[54] SPHYGMOMANOMETER

[75] Inventor: Tomohiro Kami, Hikone, Japan

[73] Assignee: Matsushita Electric Works, Ltd., Osaka, Japan

[21] Appl. No.: 596,261

[22] Filed: Apr. 3, 1984

[30] Foreign Application Priority Data

Jun. 15, 1983 [JP] Japan .................... 58-106890

[51] Int. Cl.⁴ .................................. A61B 5/02
[52] U.S. Cl. ........................ 128/686; 128/327
[58] Field of Search ........ 128/686, 672, 677, 680–683, 128/327

[56] References Cited

U.S. PATENT DOCUMENTS

| 2,753,863 | 7/1956 | Bailey ........................... 128/686 X |
| 3,557,779 | 1/1971 | Weinstein ........................ 128/682 |
| 3,633,567 | 1/1972 | Sarnoff .......................... 128/686 |
| 4,248,242 | 2/1981 | Tamm ............................ 128/678 |
| 4,308,871 | 1/1982 | Shouda et al. .................... 128/686 |
| 4,429,699 | 2/1984 | Hatschek ........................ 128/686 X |

FOREIGN PATENT DOCUMENTS

| 2220233 | 5/1978 | Fed. Rep. of Germany ...... 128/686 |
| 2837707 | 3/1980 | Fed. Rep. of Germany ...... 128/686 |
| 518687 | 7/1949 | Japan . |
| 1441832 | 7/1976 | United Kingdom ............... 128/686 |
| 0655385 | 4/1979 | U.S.S.R. ........................... 128/686 |

Primary Examiner—Lee S. Cohen
Assistant Examiner—Angela D. Sykes
Attorney, Agent, or Firm—Koda and Androlia

[57] ABSTRACT

An easy adaptable sphygmomanometer having display means for indication of the user's blood pressure is disclosed herein. The sphygmomanometer comprises a main body having thereon the display means, an arm engageable resilient retainer connected to the underside of the main body for retaining such main body in positive arm engaging disposition on a single arm of the user, and a wrap-around cuff carried by the retainer and provided with an inflatable bag which extends along the interior circumference of the retainer. The arm engaging resilient retainer is curved to be arcuate in cross section so as to insure a friction fit engagement with the arm, whereby the main body can be retained in place until the final or complete fitting of the cuff around the arm of the user. Accordingly, the display means on the main body will not require any further adjustment of its position and can be kept at a prominent position to be easily observed by the user oneself, rendering the instrument ready for measuring the user's own blood pressure.

4 Claims, 5 Drawing Figures

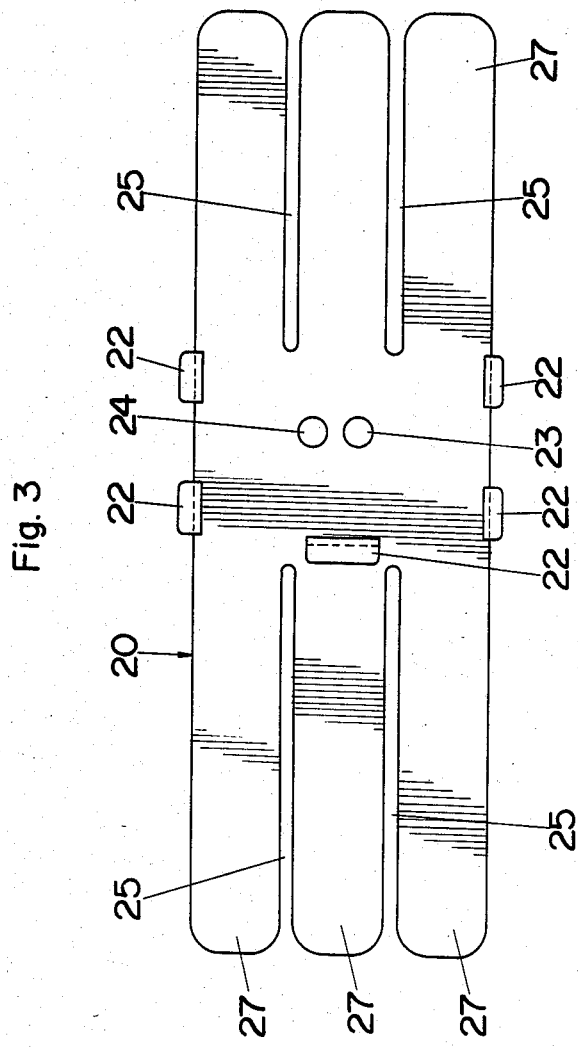

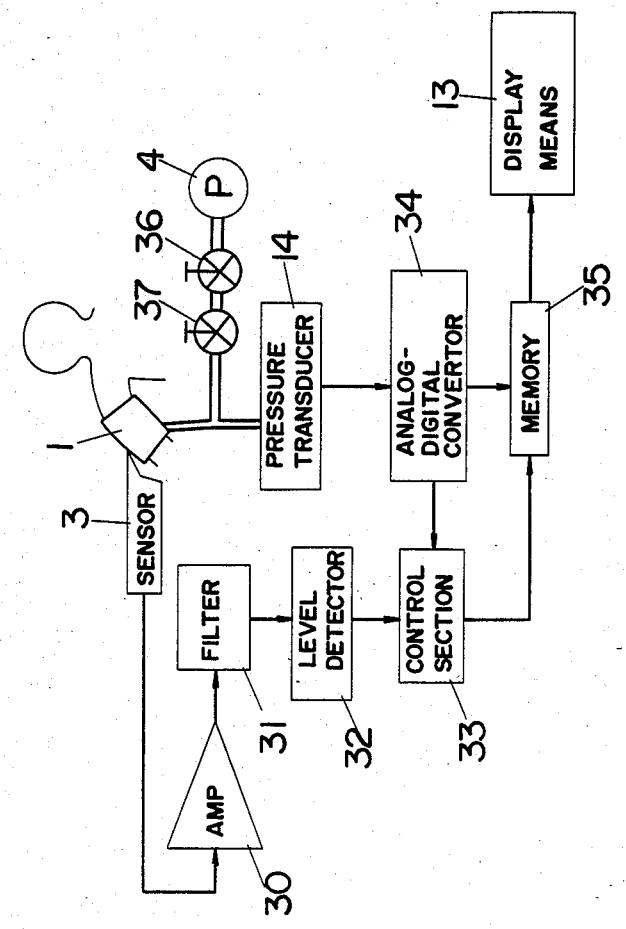

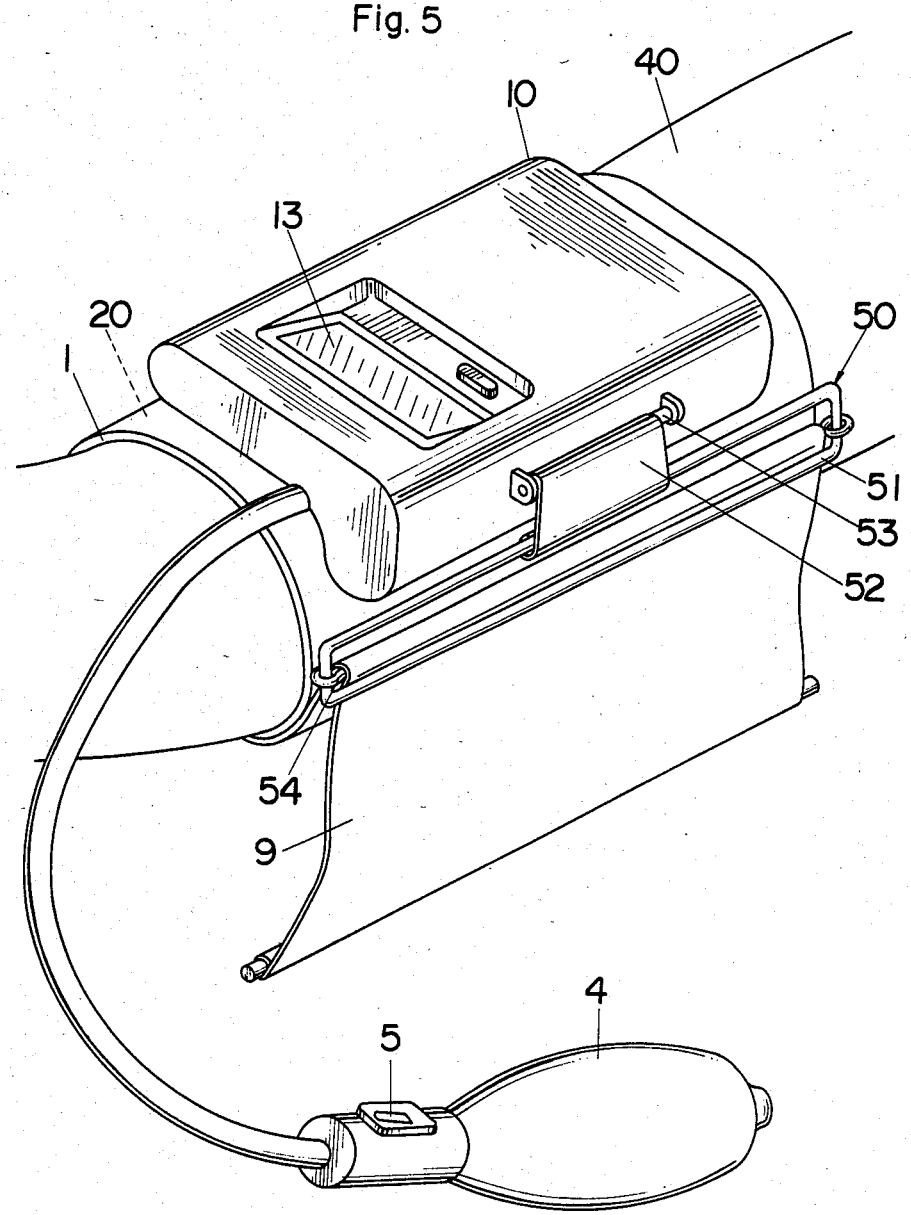

SPHYGMOMANOMETER

BACKGROUND OF THE DISCLOSURE

1. Fields of the Invention

This invention is directed to a sphygmomanometer utilized in the measuring of a person's blood pressure based on listening for Korotkoff sounds, particularly to a sphygmomanometer of the type adapted for use in measuring the blood pressure of the user by oneself.

2. Description of the Prior Art

One known sphygmomanometer of this type has been proposed in Japanese Utility Model Early Publication (KOKAI) No. 51-8687 in which a cuff is secured to a main body or housing accommodating means for detecting and indicating a user's blood pressure. In taking the blood pressure by the use of this instrument, the cuff is required to be wrapped around the user's arm extended generally horizontally in such a manner as to place the main body on the arm with its upper surface facing upwardly for the purpose of arranging a manometer on the upper side of the main body to be readily observed by the user oneself. However, due to the inherent nature of the main body being in heavy construction, the main body is likely to slip down on the backside of the arm or to be shifted from the correct position prior to complete or tight fitting of the cuff around the arm. To prevent such accidental slippage, it has been a normal practice with this sort of the instrument to firstly wrap the cuff around the arm rather loosely and then bring the main body into the correct position where the manometer is readily viewed by the user and finally tighten the cuff for a subsequent blood pressure detecting operation. As above, this procedure is rather cumbersome and therefore renders this instrument to be rather difficult to handle. Alternatively, it may be possible to extend the user's arm into the loop of the cuff already formed by fastening the opposite ends thereof prior to adapting the instrument on the user's arm, but this procedure will also suffer a problem that the main body is not expected to be stable on the arm until the cuff is tightly wrapped around the arm. That is, the above prior instrument fails to be in positive engaging disposition on the arm during the tightening operation of the cuff when wrapping the cuff with the main body resting on the arm or even when extending the arm in the loop of the cuff, and therefore requires a special technique which requires a certain degree of skill acquired only after extended practice or a troublesome procedure for retaining the main body in the correct position until the complete fitting of the instrument on the arm of the user. The sphygmomanometer instrument having a cuff attached to the main body and shaped in the form of a loop is disclosed in U.S. Pat. No. 4,248,242 patented to Tamm. The above shortcomings are also present in this prior art instrument.

In the meanwhile, prior sphygmomanometers incorporating a sound sensor to listen for Korotkoff sounds have in almost all cases an indication of the position of the sensor such that the user can easily adjust the sensor in a correct coincident position with the artery in the arm around which the cuff is wrapped. But, unfortunately there is the fact on the other side that the users who are unfamiliar with the blood pressure measuring scarcely have the knowledge of the exact position of the artery in their arms, so that there frequently occurs a serious failure in the positioning of the sensor, resulting in inaccurate measurement of the blood pressure.

Further, in the instrument disclosed in the above Japanese Utility Model Publication, there is a fear that the one end of the cuff when wrapped around a slender arm may extend on the upper surface of the main body to such an extent as to overlap or conceal the manometer.

SUMMARY OF THE INVENTION

The above shortcomings and disadvantages associated with the prior art sphygmomanometers have been eliminated by the present invention which comprises a main body or housing having thereon display means indicating the blood pressure to be detected, an arm engaging resilient retainer connected to the underside of the main body for retaining such main body in positive arm engaging disposition on a single arm of the user, and a wrap-around cuff carried by said retainer and provided with an inflatable bag which extends circumferentially along the inside of the retainer. Said arm engaging resilient retainer is curved to be arcuate in cross section so as to insure a friction fit engagement with the arm. This enables the main body to be retained until the complete fitting of the cuff around the arm at such a proper position on the arm that the display means is readily observed by the user oneself, that is, the main body can be prevented from shifting accidentally during the tightening or inflating operation of the cuff around the arm.

Accordingly, it is a primary object of the present invention to provide a sphygmomanometer capable of being readily and securely fit on the arm of the user with the display means being kept at a prominent position to be readily observed by the user oneself.

The main body accommodates judging means which responds to Korotkoff sounds monitored by a sound sensor to determine the blood pressure and display it on the display means. The main body or housing has on its bottom wall an arcuate section which extends along one part of the periphery of the retainer to fit thereon. Said arcuate section of the bottom wall cooperates with the top wall of a generally flat shaped top wall of the housing to define a relatively deep space extending below the plane including the juncture of the apex of the retainer and the bottom wall of the housing, such space being utilized for receiving an electric battery for operating said judging means, sound sensor and the display means. Thus, the electric battery requiring a relatively larger space can be accommodated without adding an extra thickness to the housing above that plane, so that the thickness of the housing projecting above that plane can be determined irrespective of the space consuming electric battery. With this space saving structural arrangement, the thickness of the housing above the apex of the retainer can be reduced to a minimum, which in turn reduces an added height of the housing and the retainer.

It is therefore another object of the present invention to provide a sphygmomanometer constructed in a reduced height enough to be completely portable and occupy little space when packed.

The arm engaging resilient retainer is in the form of a generally C-shaped split loop with an axially extending opening. The sound sensor is incorporated in the inflatable bag of the cuff at a position about 45 degrees spaced angularly about a center axis of the retainer with respect to a line passing through the center axis and the general plane of the housing at a right angle thereto. This angularly displaced location of the sound sensor is particularly useful and advantageous for easy coincidence of the sound sensor with the target artery in the upper arm to be wrapped by the cuff. The artery in the upperarm of the human to be occluded by the inflatable bag of the cuff is known to exist normally at the position inside the front of the upper arm and about 45 degrees spaced angularly about a middle point of the upper arm from the front end thereof. Therefore, the sound sensor can be automatically set in an exact coincident position with the target artery simply by placing the main body or the housing horizontally on the upper arm of the user, such horizontal positioning being easily attained by the function of the above arm engaging resilient retainer. With the result of this, even the user who is unfamiliar with the position of the artery in the arm can perform an exact measurement of one's own blood pressure without paying a particular attention to the positioning of the sound sensor. In addition, the sound sensor corresponds to the intermediate portion of the inflatable bag which extends along substantially the entire circumference of the arm engaging resilient retainer and it is spaced about 180 degrees circumferentially from the opening of the retainer, so that the intermediate portion of the inflatable bag will come into a coincident position with the target artery, by which the artery is effectively occluded for the measurement of the blood pressure so as to effect the blood pressure measurement in a more accurate manner.

It is therefore a further object of the present invention to provide a sphygmomanometer which assures an easy and accurate measurement of the blood pressure.

It is frequently seen that the thickness or diameter of the upper arm to be wrapped by the cuff varies along the length thereof. Therefore, if such upper arm is embraced by a C-shaped retainer with its end portions on both sides of its opening being continuously extending axially to have a uniform diameter along the axial length thereof, there would appear an undesirable gap at the portion of a smaller diameter between the arm and the retainer, making it difficult to fit the inflatable bag properly on the arm. The present invention has been also devised to overcome the above shortcoming by a unique and advantageous configuration of the arm engageable resilient retainer in which the retainer is formed with a plurality of axially arranged and circumferentially extending slits, one end of each slit terminating at said opening of the retainer so as to divide the circumferential ends of the retainer into a plurality of resilient wings capable of flexing relatively freely from the adjacent ones. With this result, all the wings can have enough resiliency to individually embrace the portions of different diameters of the arm to provide no substantial gap between the retainer and the arm, such that the inflatable bag inside the retainer can be properly and effectively fitted on the upper arm of the user.

It is therefore a still further object of the present invention to provide a sphygmomanometer in which the inflatable bag can be suitably wrapped around the upper arm irrespective of the difference appearing in the diameter between the longitudinal ends of the portion of the upper arm to be wrapped by the cuff.

In a preferred embodiment of the present invention, fastening means is provided on the cuff for holding the cuff in a fixed position of being wrapped around the arm of the user. The fastening means comprises an adjustable buckle slidably mounted on the cuff and a shackle provided on the buckle to be engageable with a holder fixed on the main body. The one end of the cuff is inserted in the buckle so as to be reversed or folded back thereat in the fixed position and is thus prevented from overlapping the main body particularly the display means.

It is therefore a more object of the present invention to provide a sphygmomanometer in which the end of the cuff will not be a hindrance to the viewing of the blood pressure indicated at the display means on the main body.

These and still other objects of the present invention will be more apparent from the following detailed description when taken in conjunction with the accompanying drawings.

BRIEF DESCRIPTION OF THE DRAWINGS

FIG. 3 is an extended view of an arm engaging retainer employed in the above sphygmomanometer;

FIG. 4 is a block diagram illustrating the function of the above sphygmomanometer; and FIG. 5 is a perspective view of the above sphygmomanometer in its actual use position on the arm of a user.

DETAILED DESCRIPTION OF THE EMBODIMENT

Figure 1:
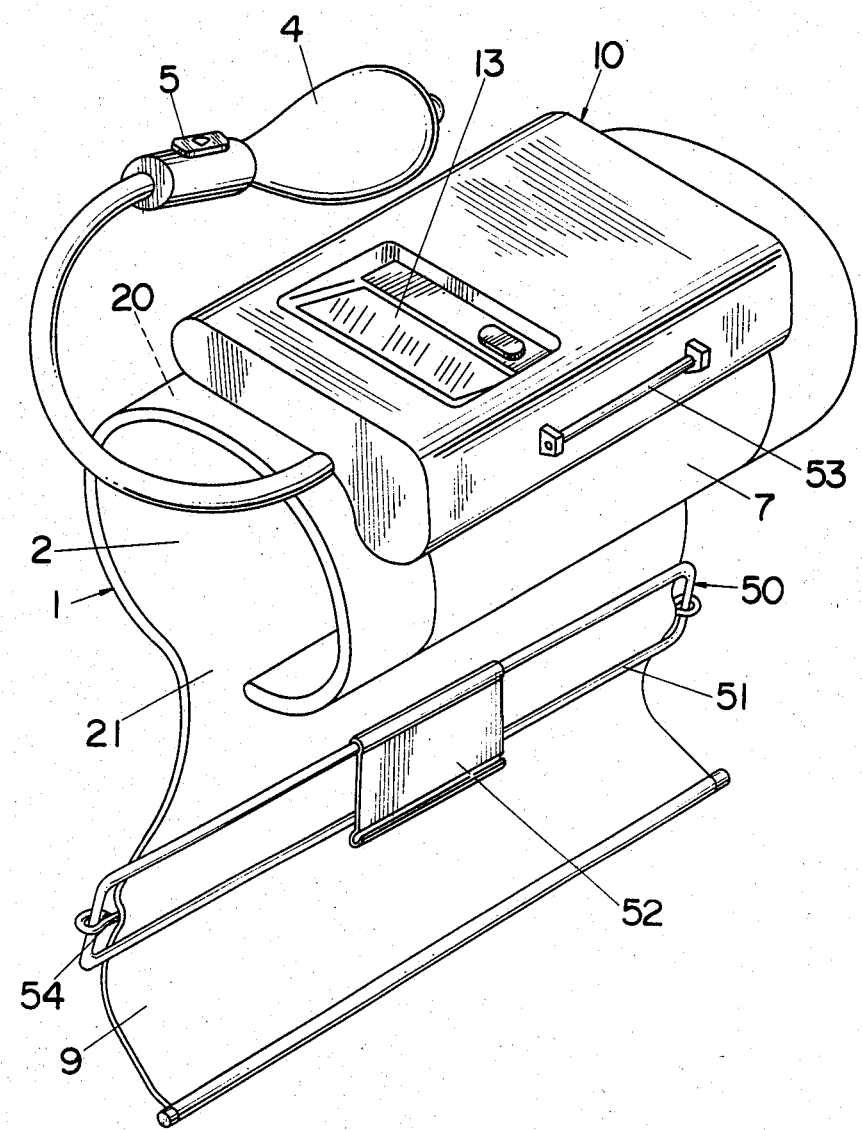
FIG. 1 is a perspective view of sphygmomanometer in accordance with a preferred embodiment of the present invention.
Figure 2:
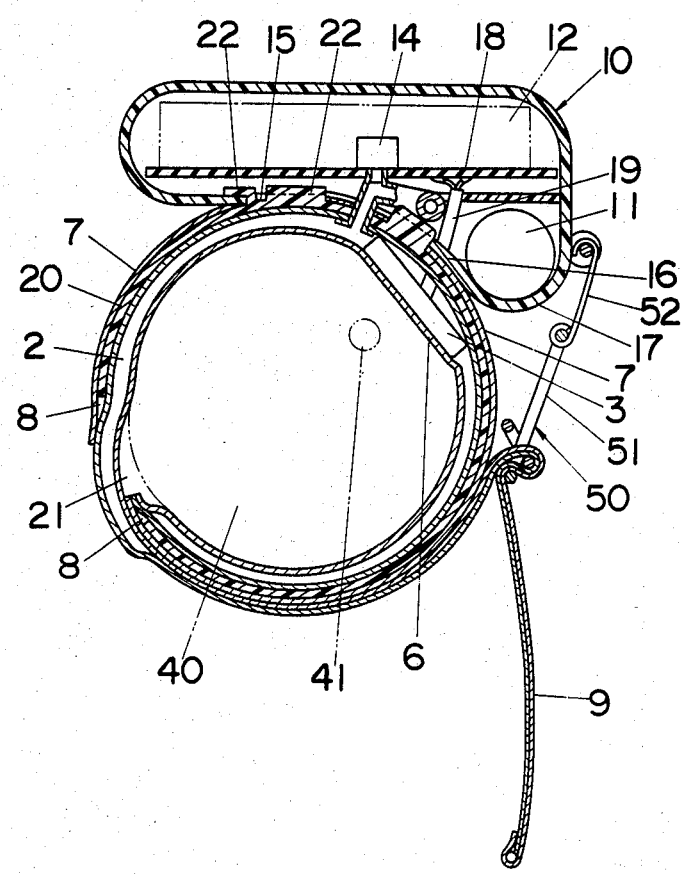
FIG. 2 is a sectional view of the above sphygmomanometer.

Referring now to FIGS. 1 and 2, a sphygmomanometer in accordance with a preferred embodiment of the present invention is composed basically of a wrap-around cuff 1, a housing 10 forming a main body to accommodate therein an electric battery 11 and an electric circuit 12 powered thereby, display means 13 mounted on the upper surface of the housing 10, and an arm engageable resilient retainer 20 for retaining the housing 10 in positive arm engaging disposition on a single upper arm 40 of the user. Said wrap-around cuff 1 incorporates within its structure an inflatable bag 2 in which a sound sensor 3 for sensing Korotkoff sounds is received and to which are connected a pressure transducer 14 disposed in the housing 10 and a squeeze bulb 4 with pressure releasing means 5. The arm engaging retainer 20 is molded from an elastic material such as nylon or polypropylene to have a generally C-shaped cross section with an axially extending narrow opening 21. Integrally formed with the retainer 20 are a set of outwardly projecting hooks 22 at the portion intermediate its circumferential ends which are inserted to corresponding slots 15 in the bottom wall of the housing 10 so as to securely connect the retainer 20 to the housing 10. Said sound sensor 3 in the inflatable bag 2 abuts intimately to a skin engaging lining 6 of the inflatable bag 2 and is connected to said electric circuit 12 in the housing 10 by means of shielded wires 19 extending through the opposite lining of the bag 2 and through an aperture 23 in the retainer 20 in such a way as to provide an airtight seal between the shielded wires 19 and the inflatable bag 2.

Extending along the outer surface of the inflatable bag 2 are a pair of jackets 7 each being bonded at its one end to each of the longitudinal ends of the bag 2 so as to form a pair of pockets 8 for receiving therein the circumferential halves of said arm engaging retainer 20 such that the inflatable bag 2 is carried by the retainer 20. Thus, the inflatable bag 2 having a length slightly longer than the circumference of the retainer 20 extends along substantially the entire circumference of the retainer 20 with one end portion extending through the opening 21 of the retainer 20 such that the remaining portion of the cuff 1 or the extension cuff 9 can be tightened on the outer side of the retainer 20.

Said housing 10 is a flat-shaped hollow member and has the display means 13 on the top wall thereof for indicating systolic and diastolic blood pressures determined by the electric circuit 12. The bottom wall of the housing 10 has an arcuate section 16 which extends along the part of the retainer 20 and curves at its one end into side wall of the housing 10 to define thereat a downwardly projecting and rounded corner portion 17, which in turn cooperates with the horizontal top wall of the housing 10 to define a relatively deep space for receiving therein said electric battery 11. In this embodiment, the arcuate section 16 terminates at the opposite end in a horizontal section of the bottom wall which extends tangentially with respect to the apex of the retainer 20, and said battery 11 is received below the plane of that horizontal section of the bottom wall, so that the battery 11 will not project upwardly of the apex of the retainer 20, leaving above the plane of horizontal section a room enough for accommodating said electric circuit 12 within a limited height or thickness. Disposed above that plane within the housing 10 is a printed circuit board 18 on which a number of electric components are mounted for constituting said electric circuit 12 which operates to determine systolic and diastolic blood pressures based on Korotkoff sounds detected by said sound sensor 3 and to indicate the blood pressure on said display means 13.

A brief explanation of the above electric circuit 12 will follow with reference to FIG. 4. The circuit 12 comprises an amplifier 30 for amplifying the noise or sound developed in the occluded artery and detected by the sound sensor 3. The output from the amplifier 30 is then fed to a level detector 32 through a filter 31 for identifying Korotkoff sounds by known methodology. When Korotkoff sound firstly appears and finally disappears, a control section 33 responds to acknowledge the values of pressures detected by said pressure transducer 14 and converted by an analogue-digital converter 34 so as to determine the systolic and diastolic pressures, which are indicated on the display means 13. A memory 35 is provided for storing temporarily the above data prior to the indication of the data on the display means 13. Said pressure releasing means 5 comprises serially connected valves in the tubing between the squeeze bulb 4 and the inflatable bag 2, one being a bleed valve 36 which allows air in the inflatable bag 2 to bleed out at a constant rate in the course of measuring the blood pressures and the other being a rapid release valve 37 for rapidly evacuating the inflatable bag 2 after the measurement.

Turning back to FIG. 2, said sound sensor 3 is arranged at a position about 45 degrees spaced circumferentially along the retainer 20 with respect to the horizontal plane or the general plane of the housing 10, whereby the sound sensor 3 will come into coincidence with the artery 41 seen normally at such an angular position about a middle point thereof spaced about 45 degrees from the front end of the upper arm of the user when he or she puts the housing 10 generally horizontally on his or her upper arm, such positioning of the housing 10 on the upper arm 40 being easily effected by the function of said arm engaging retainer 20. That is, due to its inherent resiliency, the arm engaging retainer 20 can be spread apart to allow the entrance of the arm through its opening 21 into the interior thereof. After the insertion of the arm, the retainer 20 will spring back to embrace the arm with the inflatable bag 2 being in contacting engagement therewith and to retain the housing 10 horizontally on the front of the upper arm. This condition will be therefore kept in the subsequent procedures of inflating the bag 2 and bleeding out the air therefrom in the measurement of the blood pressure. There may be miscoincidence of the sensor 3 with the artery 41 depending upon the thickness or diameter of the upper arm or possible inclination of the housing 10 at the time of placing the housing 10 on the arm. However, such miscoincidence is found to be less so as not to bring about a substantial decrease in effective measurement of the Korotkoff sounds. Thus, the user is only required for the alignment of the sensor 3 with one's artery to simply place the housing 10 horizontally on the front of one's upper arm. This position of the housing 10 is also preferable for easy recognition of the display means 13 by the user oneself. Therefore, placing the housing 10 on the upper arm in such a manner as to locate the display means 13 in an easy recognition position will automatically effect the exact alignment of the sensor 3 with the artery 41 to be occluded, enabling the user to handle the instrument without a particular attention to such alignment.

In connection with the above, the sound sensor 3 arranged in a coincident disposition with the artery 41 is also in a location to be opposed diametrically to the opening 21 of the retainer 20, such that the intermediate portion of the inflatable bag 2 extending along substantially the entire circumference of the retainer 20 can correspond to the artery 41, rendering effective occlusion or compression of the artery 41 by the inflatable bag 2.

Referring to FIG. 3, said retainer 20 is formed with pairs of slits 25, the slit 25 in each pair extending longitudinally or circumferentially of the retainer 20 in a parallel relationship with one another and terminating at each longitudinal end to divide each longitudinal end portion into resilient wings 27 which are capable of being flexed relatively freely or rather independently. When the retainer 20 is engaged with the upper arm having an appreciable difference in the diameter along the length thereof, the resilient wings 27 serve to embrace the corresponding segments of the arm whereby the whole retainer 20 can fit readily on such arm without producing a substantial gap between the retainer 20 and the portion of a smaller diameter of the arm. With this result, the inflatable bag 2 is prevented from inflating outwardly to such a large extent so as to apply effectively the compressing pressure onto the arm wrapped thereby. In the above figure, numeral 23 designates an aperture through which the shielded wires 19 from the sensor 3 extends and numeral 24 designates an aperture through which the tubing leading to said pressure transducer 14 extends.

The cuff 1 is provided at its extension 9 from the inflatable bag 2 with fastening means 50 for holding the cuff 1 in a fixed position of being wrapped around the arm of the user. The fastening means 50 is composed of an adjustable buckle 51 slidably mounted on the extension cuff 9 and a shackle 52 carried on the buckle 51 to be engageable with a holder 53 in the form of a rod fixed to the side of the housing 10. The buckle 51 is formed of a rectangular frame and a center bar 54 bridging the opposite side of the frame with its end portions slidably engaged therewith. The extenions cuff 9 extends through the openings of the frame on both sides of the center bar 54 so as to slidably carry the buckle 51. The shackle 52 has its one end pivoted to the frame of the buckle 51 and has a hook at the opposite end. With the use of this fastening means 50, the user after placing the housing 10 on the front of the upper arm can easily tighten the cuff 1 therearound simply by hooking the shackle 52 followed by pulling the free end portion of the extension cuff 9 downwardly. At this condition as illustrated in FIG. 5, the extension cuff 9 will hang down so as not to overlie the housing 10, eliminating the possibility of concealing the display means 13 by the extension cuff 9 and thus providing easy reading of the pressure values indicated thereat in the subsequent measurement of the blood pressures beginning with pumping up the inflatable bag 2. For disengaging the cuff 1 from the arm after the blood pressure measurement, the center bar 54 is pushed up to loosen the cuff 1 and to unhook the shackle 52.

The above description and particularly the drawings are set forth for purposes of illustration only. It will be understood that many variations and modifications of the embodiments herein described will be obvious to those skilled in the art, and may be carried out without departing from the spirit and scope of the invention.

What is claimed is:

1. A sphygmomanometer comprising:
    a main body having thereon display means for indicating the blood pressure detected thereby;
    an arm engaging resilient retainer connected to a bottom wall of the main body for retaining such main body in positive arm engaging disposition on a single arm of the user, said arm engaging resilient retainer being curved to be arcuate in cross section to be adapted to the arm, said arm engaging resilient retainer further being formed with a plurality of circumferentially extending slits which divide the end portions on both sides of the retainer into a plurality of resilient wings capable of flexing relatively freely;
    a wrap-around cuff carried by said retainer and provided with an inflatable bag which extends along the circumference of the inside of said resilient retainer and which incorporates therein a sound sensor, said sound sensor being connected to the display means; and
    fastening means provided on the cuff for holding the cuff in a fixed position of being wrapped around the arm of the user.

2. A sphygmomanometer as set forth in claim 1, wherein said bottom wall of the main body has an arcuate section which extends along the periphery of said retainer to fit thereon, said arcuate section cooperating with a generally flat shaped top wall of the main body to define a relatively deep space therebetween for receiving therein an electric battery for operating the sphygmomanometer and wherein said retainer is formed with projecting hooks at a portion intermediate its circumferential end and said hooks are coupled to the bottom wall of the main body.

3. A sphygmomanometer as set forth in claim 1, wherein said arm engaging retainer is in the form of a generally C-shaped split loop with an axially extending opening and wherein said sound sensor is disposed at a position about 180 degrees spaced circumferentially along the retainer from the opening and at the same time about 45 degrees spaced angularly about the center of the retainer relative to the main body which in use extends horizontally.

4. A sphygmomanometer as set forth in claim 1, wherein said fastening means comprises an adjustable buckle slidably mounted on the cuff and a shackle provided on the buckle to be engageable with a holder fixed on the main body.

* * * * *